United States Patent
Cai et al.

(10) Patent No.: US 11,039,587 B2
(45) Date of Patent: Jun. 22, 2021

(54) POLYPLOID RICE TWO-LINE RESTORER LINE AND BREEDING METHOD THEREOF

(71) Applicants: WUHAN POLYPLOID BIOTECHNOLOGY CO., LTD, Hubei (CN); HUBEI UNIVERSITY, Hubei (CN)

(72) Inventors: Detian Cai, Hubei (CN); Zhaojian Song, Hubei (CN); Xianhua Zhang, Hubei (CN); Yuhua Liu, Hubei (CN); Wei Wang, Hubei (CN); Yuchi He, Hubei (CN)

(73) Assignees: WUHAN POLYPLOID BIOTECHNOLOGY CO., LTD., Hubei (CN); HUBEI UNIVERSITY, Hubei (CN)

( * ) Notice: Subject to any disclaimer, the term of this patent is extended or adjusted under 35 U.S.C. 154(b) by 361 days.

(21) Appl. No.: 15/926,239

(22) Filed: Mar. 20, 2018

(65) Prior Publication Data

US 2018/0206424 A1    Jul. 26, 2018

Related U.S. Application Data

(63) Continuation of application No. PCT/CN2017/095933, filed on Aug. 4, 2017.

(30) Foreign Application Priority Data

Sep. 29, 2016    (CN) .......................... 201610864023.6

(51) Int. Cl.

| | |
|---|---|
| *A01H 1/02* | (2006.01) |
| *A01H 1/04* | (2006.01) |
| *A01H 6/46* | (2018.01) |
| *A01H 4/00* | (2006.01) |
| *A01H 1/08* | (2006.01) |
| *A01H 5/10* | (2018.01) |

(52) U.S. Cl.
CPC ................. *A01H 1/02* (2013.01); *A01H 1/04* (2013.01); *A01H 1/08* (2013.01); *A01H 4/008* (2013.01); *A01H 5/10* (2013.01); *A01H 6/46* (2018.05); *A01H 6/4636* (2018.05)

(58) Field of Classification Search
CPC ................................ A01H 1/04; A01H 6/4636
See application file for complete search history.

(56) References Cited

FOREIGN PATENT DOCUMENTS

| | | |
|---|---|---|
| CN | 1058129 A | 1/1992 |
| CN | 1266615 A | 9/2000 |
| CN | 101326895 A | 12/2008 |
| CN | 103444511 A | 12/2013 |
| CN | 104026006 A | 9/2014 |
| CN | 106561443 A | 4/2017 |
| WO | 2013124844 A1 | 8/2013 |

OTHER PUBLICATIONS

Cai, D. et al. Science in China Series C: Life Sci (Jun. 2007)) vol. 50, No. 3; pp. 356-366. (Year: 2007).*
Zuo, Bo, "Studies on the Fertility and combination of CMS Lines and Recovery lines of Polyploid Rice", China Excellent Master's Dissertation Database Agricultural Science and Technology, vol. 15.07.2013, A Thesis Submitted for the Degree of Master, Hubei University, pp. 1-67, Wuhan China, Presented: May 20, 2012.
Cai, Detian et al., "The breeding of two polyploid rice lines with the characteristic of polyploid meiosis stability", Science in China Series C: Life Sciences, vol. No. 50, Issue No. 3, pp. 356-366, Jun. 2007.

* cited by examiner

*Primary Examiner* — Russell Kallis
(74) *Attorney, Agent, or Firm* — Tim Tingkang Xia, Esq.; Locke Lord LLP

(57) ABSTRACT

A breeding method of a polyploid rice two-line restorer line includes determining hybrid parents for breeding the restorer line; breeding a restorer line of an indica sterile/japonica restorer type, or breeding a restorer line of a japonica sterile/indica restorer type, and carrying out backcrossing or composite hybridization after hybridization of the parents; selecting a single plant that meets the breeding goal, carrying out composite hybridization again and carrying out preliminary molecular marker detection; comparing, and selecting a single plant with good traits for continuous selfing until the line is basically stable; selecting a stable line with good traits and detection molecular markers; carrying out test-crossing on the preferred line as a male parent with different types of polyploid sterile lines; and selecting a good hybrid combination and a restorer line thereof.

3 Claims, 7 Drawing Sheets

POLYPLOID RICE TWO-LINE RESTORER LINE AND BREEDING METHOD THEREOF

CROSS-REFERENCE TO RELATED APPLICATIONS

This application is a continuation application of International Patent Application No. PCT/CN2017/095933, filed Aug. 4, 2017, which itself claims priority to Chinese Patent Application No. 201610864023.6, filed Sep. 29, 2016 in the State Intellectual Property Office of P.R. China, which are hereby incorporated herein in their entireties by reference.

FIELD OF THE INVENTION

The present invention relates generally to the field of new crop variety breeding of modern agriculture, and more particularly to a polyploid rice two-line restorer line and a breeding method thereof

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. At present, rice planted all over the world is diploid, that is, it contains only two sets of chromosomes in cells, 2n=2X=24. After the first green revolution from high-stalk varieties to short-stalk varieties and the second green revolution from conventional rice varieties to hybrid rice varieties, the rice yield has increased significantly. Since the mid-1980s, the rice yield is in a high-yielding stable period for a long time, with a yield-increasing rate of no more than 5% among breeding varieties within various years, which is difficult to meet the goal of yield-increasing percentage of 50% after 2050, to ease the world food crisis. For this reason, Cai Detian, Yuan Longping, et al. (2001) proposed a new strategy of "breeding super rice by distant hybridization and polyploid double superiority" from the perspective of evolutionary biology; just like wheat, cotton and oilseed rape, evolving from diploid wild species to the cultivated tetraploid or hexaploid species that doubles the yield, to breed polyploid rice with four or six sets of chromosomes that have the potential to increase the yield by 50%, and fundamentally ease the world food crisis. In particular, the use of polyploid "two-line" hybrid rice is the first stage of the three stages of polyploid rice breeding. "Two-line" is the abbreviation of photo-thermo-sensitive genetic male sterile line and the restorer line (relative to the "three lines": male sterility line, male sterile maintainer line and male sterile restorer line). The male reproductive organ of the photo-thermo-sensitive genetic male sterile line shows difference in sterility or fertility under different light (long day, short day) or different temperature (high temperature, low temperature), and the same plant can transform from sterility to fertility. The transformation of sterility and fertility makes a line have the characteristics of "sterile line" and "maintainer line". It can be bred with a restorer line during the sterile period and can be propagated during the fertile period, to achieve the purpose of "one line for two uses". The restorer line is short for male sterility restorer line, which refers to that the plant male and female organs develop normally and pollinate and seed normally by themselves. Moreover, pollens thereof can pollinate male sterile lines for seeding and restore normal fertility of the hybrid generations of pollens for selfing and seeding, and thus called restorer line. Therefore, the polyploid restorer line is firstly a polyploid, for example, tetraploid rice is 4X=48; then the polyploid restorer line has the characteristics of stout stalks, large floral organs, large spikes and big grains, great pollen quantity, large pollen grains and normal black color of $I_2$-KI, etc. It can seed by selfing; pollens thereof can pollinate male sterile lines to seed as a hybrid; the first generation of hybrid can also seed normally, to show strong heterosis, so that the existing diploid heterosis is transformed to a new approach of polyploid heterosis utilization. In addition, it can overcome the incompatibility of hybridization between indica and japonica subspecies, with greater potential for yield increase and resistance, so it is of great significance to solve the world food crisis.

Therefore, a heretofore unaddressed need exists in the art to address the aforementioned deficiencies and inadequacies.

SUMMARY OF THE INVENTION

An objective of the present invention is to provide a breeding method of a polyploid rice two-line restorer line.

Another objective of the present invention is to provide a polyploid rice two-line restorer line.

To achieve the objectives, the present invention adopts the following technical solutions:

A breeding method of a polyploid rice two-line restorer line comprises the following steps:

a) determining hybrid parents for breeding the restorer line, wherein the hybrid parents should comprise a PMeS (polyploid meiosis stability) gene line, a restorer line that can restore a photo-thermo-sensitive genetic male sterile gene, and indica and japonica lines that have certain resistance;

b) breeding a restorer line of an indica sterile/japonica restorer type: firstly carrying out hybridization on a tetraploid indica line as a female parent and a tetraploid japonica line having PMeS gene as a male parent, and then carrying out backcrossing or composite hybridization by using a tetraploid japonica line as a male parent; or breeding a restorer line of a japonica sterile/indica restorer type: firstly carrying out hybridization on the tetraploid japonica line as a female parent and the tetraploid indica line having PMeS gene as a male parent, and then carrying out backcrossing or composite hybridization by using a tetraploid indica line as a male parent;

c) selecting a rice single plant that meets the breeding goal in a targeted manner according to the polyploid rice ideal plant type and the characteristics of large spikes and big grains of polyploid rice, then carrying out composite hybridization on the selected rice single plant and a fine line of tetraploid rice having PMeS gene, and carrying out preliminary screening on the composite hybridization progeny by using molecular marker detection;

d) comparing the different lines selected, and selecting a single plant with good traits for continuous selfing until the traits of the line are basically stable;

e) comparing different selected lines obtained in step d), and carrying out molecular marker detection again, to select a stable line with high yield performance, good traits of spikes and grains, strong resistance and molecular markers as a preferred line;

f) carrying out test-crossing on the preferred line as a male parent with different types of polyploid rice genetic male sterile lines;

g) carrying out floristic comparison on different test-crossing group hybrids, and selecting a hybrid combination with good shape, strong resistance, strong combining ability and strong heterosis and a restorer line thereof through detections of morphological characteristics, combining ability and heterosis, wherein the restorer line is a tetraploid rice two-line restorer line;

h). submitting the selected hybrid combination including a sterile line, a restorer line and a hybrid for appraisal and regional trials; and i) applying for cultivar assessment of the tetraploid rice two-line restorer line.

In the aforesaid solutions, the tetraploid indica line in step b) is an indica restorer line that has certain resistance and can restore a photo-thermo-sensitive genetic male sterile gene; the tetraploid japonica line having PMeS gene is selected from PMeS-1 (Sg99012) and PMeS-2 (HN2026); and the tetraploid japonica line for composite hybridization is a japonica restorer line that has certain resistance and can restore the photo-thermo-sensitive genetic male sterile gene.

In the aforesaid solutions, the tetraploid japonica line in step b) is a japonica restorer line that has certain resistance and can restore the photo-thermo-sensitive genetic male sterile gene; the tetraploid indica line having PMeS gene is selected from DTS Xuan 59, DTS Xuan 32, DTS Xuan 68 and DTS Xuan 15; and the tetraploid indica line for composite hybridization is an indica restorer line that has certain resistance and can restore the photo-thermo-sensitive genetic male sterile gene.

In the aforesaid solutions, the fine line of tetraploid rice having PMeS gene is selected from HN172, HN184, HN054, HN269, HN362, T1, T3, T56, A1 and A3.

In the aforesaid solutions, the tetraploid rice two-line restorer line is screened through detections of molecular markers related to high fecundity, disease resistance, insect resistance, drought resistance and quality of rice.

A tetraploid rice two-line restorer line obtained by the breeding method of the aforesaid polyploid rice two-line restorer line is named PRXXX, wherein XXX is a figure, the tetraploid rice two-line restorer line has the characteristics of moderate plant type, high tillering ability, thick stalks, large spikes and big grains, high quality, strong resistance and average seed setting rate of 80% or more. All rice lines involved in the breeding method of the present invention are existing disclosed rice lines.

Tetraploid japonica line Dure: A tetraploid japonica rice formed by doubling the hybrid progeny of the wide compatible rice varieties Dular and C27 (presented by researcher Yang Zhenyu from Shenyang Academy of Agricultural Sciences).

PMeS-1 (Sg99012): A polyploid rice line PMeS-1 with tetraploid meiosis stability (PMeS) bred from the polyploid progenies of indica and japonica hybrids by College of Life Sciences of Hubei University through several years of indica japonica hybridization and back-crossing selection and detection, published in the journal "Cai Detian, Chen Jianguo, Chen Dongling, et al. Breeding of two polyploid rice lines with polyploid meiosis stability. Science China, 2007, 37 (2): 217-226".

PMeS-2 (HN2026): A tetraploid rice line PMeS-2 with polyploid meiosis stability (PMeS) bred from the polyploid progenies of indica and japonica hybrids by College of Life Sciences of Hubei University, published in the journal "Cai Detian, Chen Jianguo, Chen Dongling, et al. Breeding of two polyploid rice lines with polyploid meiosis stability. Science China, 2007,37 (2): 217-226".

DTS170: Tetraploid indica rice bred through chromosome doubling of the hybrid progeny of rice variety "Jiguang No. 4" by College of Life Sciences of Hubei University.

DTS Xuan 59, DTS Xuan 32, DTS Xuan 68 and DTS Xuan 15: Polyploid rice lines bred by DTS 170 and "non-threshing indica glutinous rice-4X" hybrid progeny.

HN172, HN184, HN054, HN269, T1, T3, T56: Derivative progeny polyploid rice lines with meiosis stability and excellent agronomic traits bred by using the polyploid rice line PMeS-1 (Sg99012) with polyploid meiosis stability as a parent by College of Life Sciences of Hubei University.

HN362, A1, A3: Derivative progeny polyploid rice lines with meiosis stability and excellent agronomic traits bred by using the polyploid rice line PMeS-2 (HN2026) with polyploid meiosis stability as a parent by the College of Life Sciences of Hubei University.

The present invention has the following beneficial effects that in the present invention, a breeding method of polyploid rice two-line restorer line is established. By combining the restoring ability of the photo-thermo-sensitive genetic male sterile gene and the high fecundity of polyploid rice with PMeS gene line, crossing, composite hybridization and back crossing of indica lines and japonica lines with good traits that can restore photo-thermo-sensitive genetic male sterile gene and PMeS gene and have certain resistance are performed, together with molecular marker detection, the fine variety of tetraploid rice restorer lines is bred. The tetraploid rice restorer line obtained in the present invention has the characteristics of moderate plant type, high tillering ability, thick stalks, large spikes and big grains, high quality, strong resistance and average seed setting rate of 80% or more.

More than 625 seeds for each of (1) the tetraploid japonica restorer line, Dure-4X, (2) the tetraploid japonica line having PMeS gene, Sg99012, (3) the tetraploid indica line, DTS Xuan 59, (4) the fine line of tetraploid rice having PMeS gene, HN172, and (5) the tetraploid rice two-line restorer line, PRO03, were stored/deposited under CCTCC Nos: P202103 on Dec. 10, 2020, P202108 on Dec. 10, 2020, P202102 on Dec. 10, 2020, P202104 on Dec. 10, 2020, and P202109 on Dec. 25, 2020, respectively, under the terms of the Budapest Treaty in the China Center for Type Culture Collection (CCTCC) at Wuhan University, Wuhan 430072, P. R. China, one of recognized International Depository Authorities (IDAs). The seeds will be irrevocably and without restriction or condition released to the public upon the issuance of a patent would satisfy the deposit requirement made herein.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Figure 1:
FIG. 1 shows a tetraploid rice two-line restorer line.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more". The word "exemplary" is used herein to mean "serving as an example, instance, or illustration". Any aspect described herein as "exemplary" is not necessarily to be construed as preferred or advantageous over other aspects. Unless specifically stated otherwise, the term "some" refers to one or more. Combinations such as "at least one of A, B, or C", "one or more of A, B, or C", "at least one of A, B, and C", "one or more of A, B, and C", and "A, B, C, or any combination thereof" include any combination of A, B, and/or C, and may include multiples of A, multiples of B, or multiples of C. Specifically, combinations such as "at least one of A, B, or C", "one or more of A, B, or C", "at least one of A, B, and C", "one or more of A, B, and C", and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The words "module", "mechanism", "element", "device" and the like may not be a substitute for the word "means". As such, no claim element is to be construed as a means plus function unless the element is expressly recited using the phrase "means for". It should also be understood that one or more steps within a method may be executed in different order (or concurrently) without altering the principles of the invention.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term are the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the disclosure.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

Typically, terms such as "about," "approximately," "generally," "substantially," and the like unless otherwise indicated mean within 20 percent, preferably within 10 percent, preferably within 5 percent, and even more preferably within 3 percent of a given value or range. Numerical quantities given herein are approximate, meaning that the term "about," "approximately," "generally," or "substantially" can be inferred if not expressly stated.

The description is now made as to the embodiments of the invention in conjunction with the accompanying drawings. It should be understood that specific embodiments described herein are merely intended to explain the invention, but not intended to limit the invention. Various modifications to these aspects will be readily apparent to those skilled in the art, and the generic principles defined herein may be applied to other aspects.

Embodiment 1

Breeding of tetraploid rice restorer line—PR147

Figure 3:
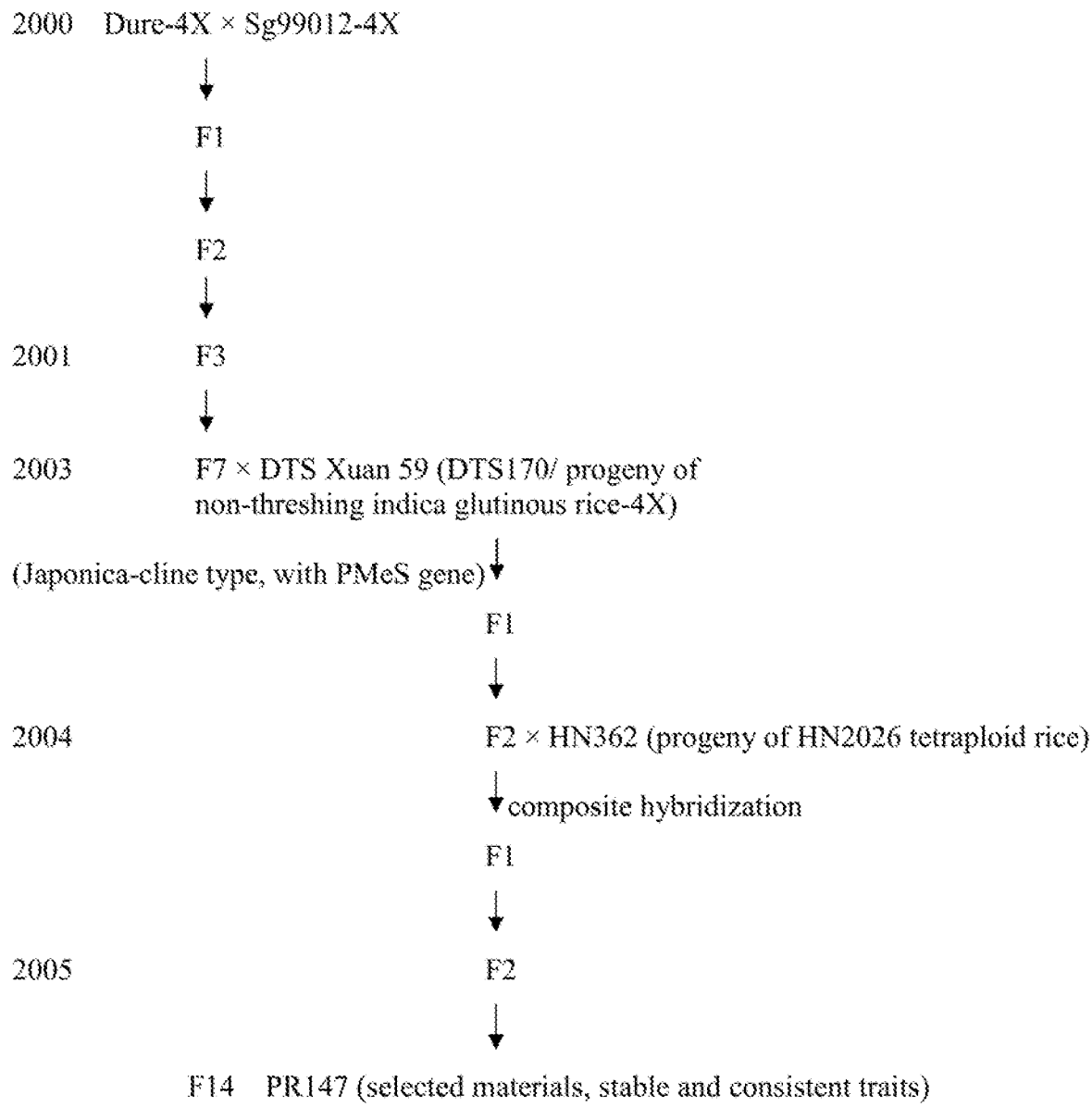
FIG. 3 shows the breeding process of the tetraploid rice restorer line—PR147.

The breeding process of the tetraploid rice restorer line—PR147, is shown in FIG. 3.

Figure 2:
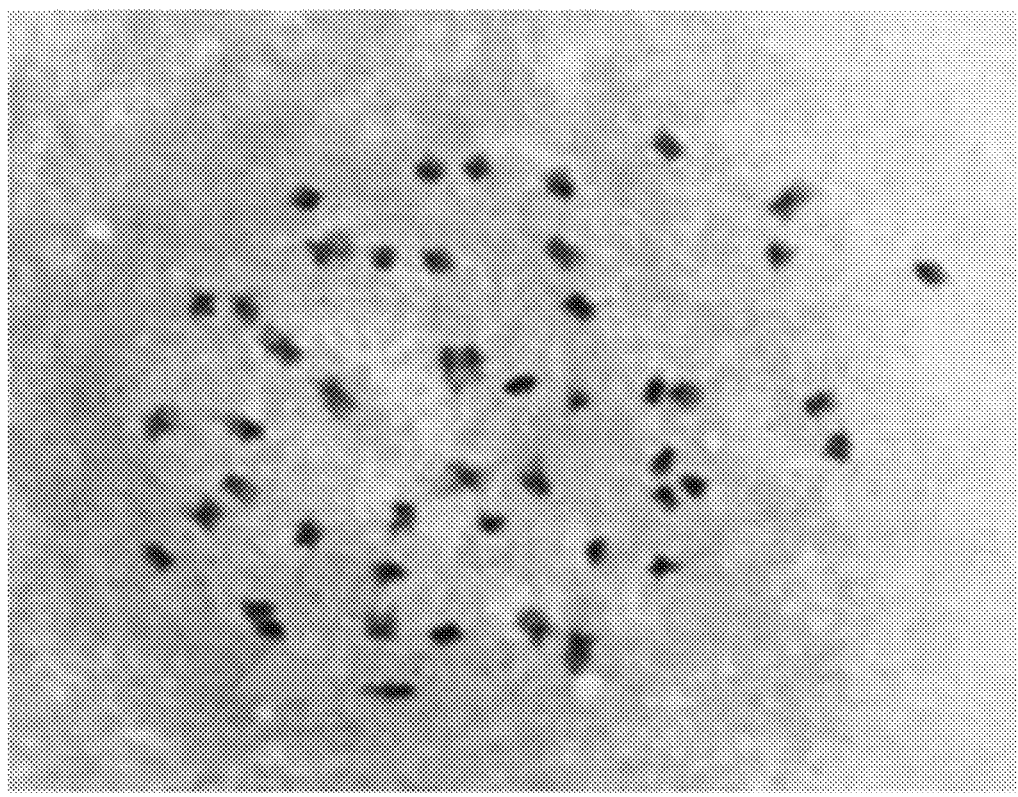
FIG. 2 shows a root tip chromosome of a tetraploid rice restorer line (2n=4x=48).

Description of Breeding Process:

The breeding method of tetraploid rice two-line restorer line—PR147, comprising the steps:
a). after clarifying the traits of the photo-thermo-sensitive two-line restorer line and the key roles of PMeS gene parents in polyploid rice breeding, determining the tetraploid rice line Dure (japonica-cline type) and the tetraploid rice line Sg99012 with PMeS gene as the original hybrid parents for breeding the restorer line;
b). carrying out hybridization on the tetraploid japonica-cline type line Dure as a female parent and the tetraploid rice line Sg99012 having PMeS gene as a male parent, and after continuous selfing of the hybrid progeny for 6 generations, then carrying out composite hybridization by using the tetraploid indica line—DTS Xuan 59 (DTS170/progeny of non-threshing indica glutinous rice) as a male parent;
c). selecting a single plant that meets the breeding goal in a targeted manner according to the polyploid rice ideal plant type and the characteristics of large spikes and big grains of polyploid rice, after selfing of composite hybridization hybrids for one generation, carrying out composite hybridization on fine line HN362 (progeny of HN2026 tetraploid rice) having PMeS gene, and then carrying out molecular marker detection screening on composite hybridization hybrids by using the molecular markers related to high fecundity, disease resistance, insect resistance, drought resistance and quality of rice;
d). after selfing and selection for multiple generations, comparing the different lines of each generation, and selecting a better single plant for continuous selfing for multiple generations until the traits of the line are basically stable;
e). comparing different selected lines, and carrying out molecular marker detection screening again by using molecular markers related to high fecundity, disease resistance, insect resistance, drought resistance and quality of rice, to select a stable line with high yield performance, good traits of spikes and grains, strong resistance and molecular markers as a preferred line;
f). carrying out test-crossing on the preferred line as a male parent with different types of polyploid rice photo-thermo-sensitive genetic male sterile lines;
g). carrying out floristic comparison on different test-crossing group hybrids, and selecting a hybrid combination with good shape, strong resistance, strong combining ability and strong heterosis and a restorer line thereof through detections of morphological characteristics, combining ability and heterosis, wherein the restorer line is a tetraploid rice two-line restorer lines, named PR147, FIG. 1 shows the picture of the tetraploid rice two-line restorer line, showing the characteristics of the tetraploid rice restorer line—moderate plant type, high tillering ability, thick stalks, large spikes and big grains, and FIG. 2 shows a root tip chromosome of the tetraploid rice restorer line (2n=4x=48);
h). submitting the selected hybrid combination including a sterile line, a restorer line and a hybrid for appraisal and regional trials; and
i). applying for cultivar assessment of the restorer line.

Embodient 2

Breeding of tetraploid rice restorer line—PR003

Figure 4:
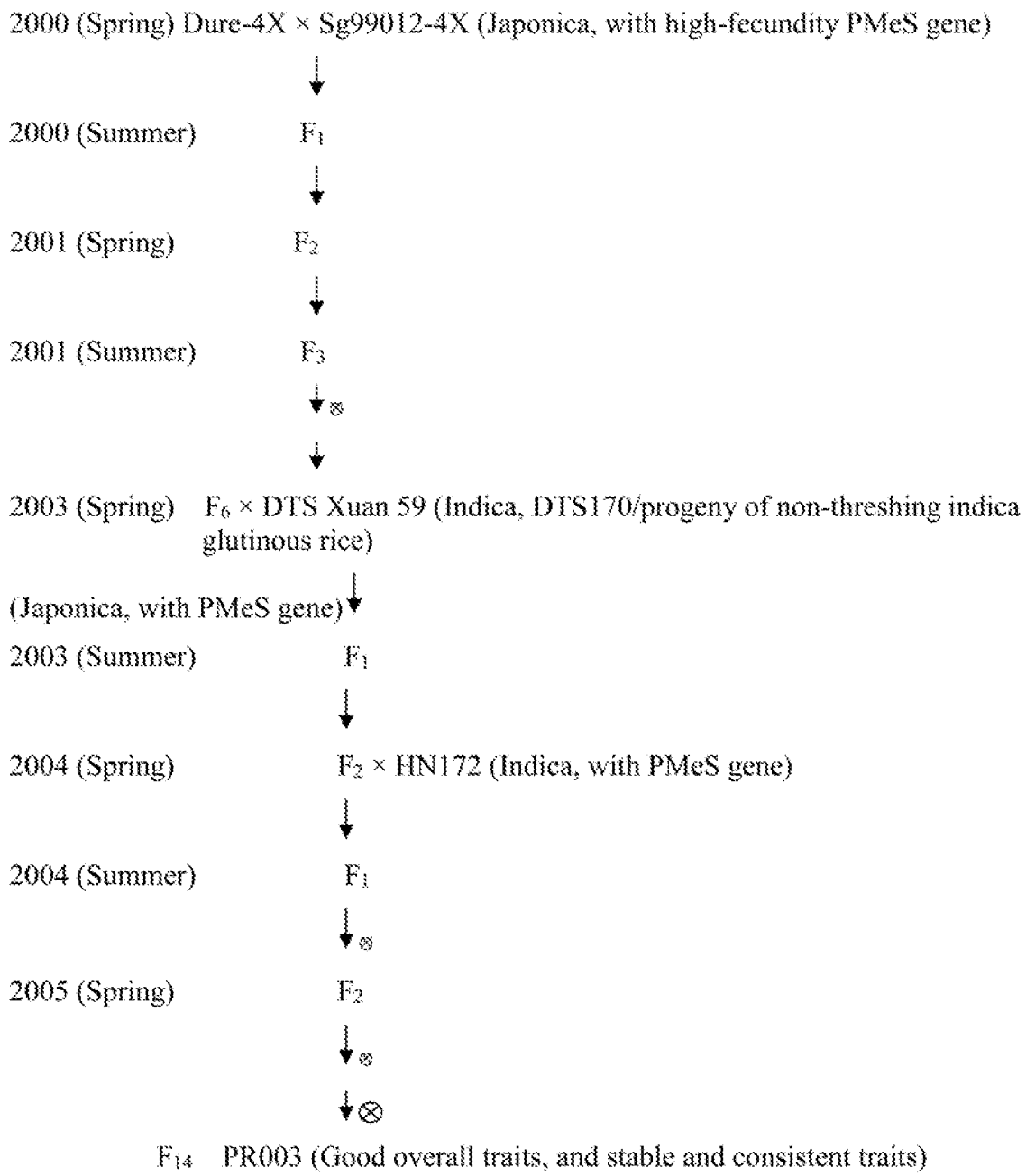
FIG. 4 shows the breeding process of the tetraploid rice restorer line—PRO03.

The breeding process of the tetraploid rice restorer line—PR003, is shown in FIG. 4.

Description of Breeding Process: The Breeding Process of Polyploid Rice Two-Line Restorer Line—PR003:
a). after clarifying the traits of the photo-thermo-sensitive two-line restorer line and the key roles of PMeS gene parents in polyploid rice breeding, determining the tetraploid rice line Dure (japonica-cline type) and the rice line Sg99012 with PMeS gene as the original hybrid parents for breeding the restorer line;
b). carrying out hybridization on the tetraploid japonica-cline type line Dure as a female parent and the tetraploid rice line Sg99012 having PMeS gene as a male parent, and after continuous selfing of the hybrid progeny for 5 generations, then carrying out composite hybridization by using the tetraploid indica line—DTS Xuan 59 (DTS170/non-threshing indica glutinous rice) as a male parent;
c). selecting a single plant that meets the breeding goal in a targeted manner according to the polyploid rice ideal plant type and the characteristics of large spikes and big grains of polyploid rice, after selfing of composite hybridization hybrids for one generation, carrying out composite hybridization on fine line HN172 having PMeS gene, and then carrying out molecular marker detection screening on the composite hybridization progeny by using the molecular markers related to high fecundity, disease resistance, insect resistance, drought resistance and quality of rice;

d). after selfing and selection for multiple generations, comparing the different lines of each generation, and selecting a better single plant for continuous selfing for multiple generations until the traits of the line are basically stable;

e). comparing different selected lines, and carrying out molecular marker detection screening again by using molecular markers related to high fecundity, disease resistance, insect resistance, drought resistance and quality of rice, to select a stable line with high yield performance, good traits of spikes and grains, strong resistance and molecular markers as a preferred line;

f). carrying out test-crossing on the preferred line as a male parent with different types of polyploid rice photo-thermo-sensitive genetic male sterile lines;

g). carrying out floristic comparison on different test-crossing group hybrids, and selecting a hybrid combination with good shape, strong resistance, strong combining ability and strong heterosis and a restorer line thereof through detections of morphological characteristics, combining ability and heterosis, wherein the restorer line is a tetraploid rice two-line restorer line, named PR003;

h). submitting the selected hybrid combination including a sterile line, a restorer line and a hybrid for appraisal and regional trials; and i). applying for cultivar assessment of the restorer line.

Embodiment 3

Figure 5:
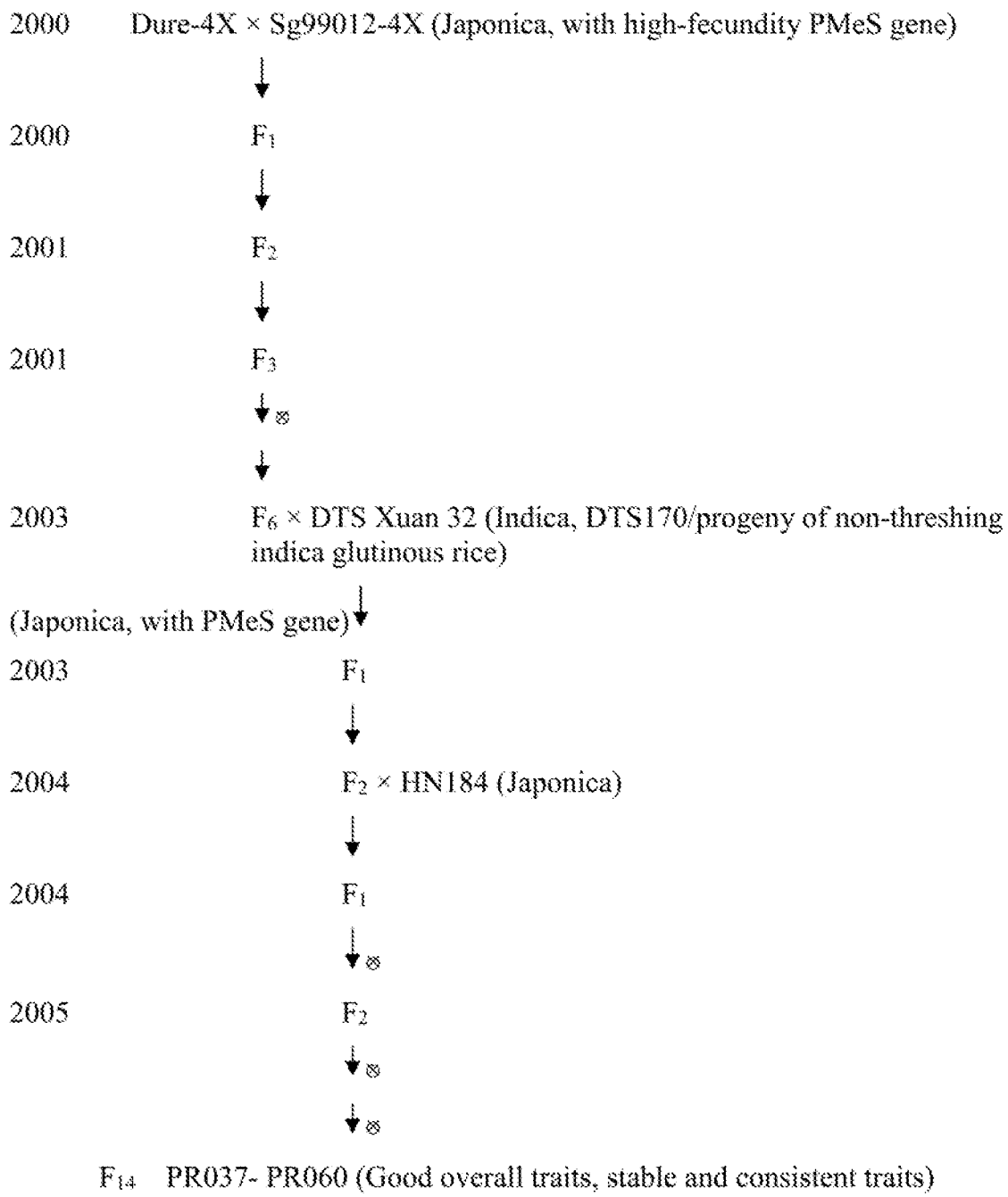
FIG. 5 shows PR037-PRO60 pedigre.

Breeding of tetrapolid rice restorer line—PR037-PR060
PR037-PR060 pedigree is shown in FIG. 5.
Description of Breeding Process:

a). carrying out hybridization on the tetraploid japonica-cline type line Dure as a female parent and the tetraploid rice line Sg99012 having PMeS gene as a male parent, and after continuous selfing of the hybrid progeny for 5 generations, then carrying out composite hybridization by using the tetraploid indica line—DTS Xuan 32 (DTS170/non-threshing indica glutinous rice) as a male parent;

b). selecting a single plant that meets the breeding goal in a targeted manner according to the polyploid rice ideal plant type and the characteristics of large spikes and big grains of polyploid rice, after selfing of composite hybridization hybrids for one generation, carrying out composite hybridization on fine line HN184 of tetraploid rice having PMeS gene, and then carrying out molecular marker detection screening on composite hybridization hybrids by using the molecular markers related to high fecundity, disease resistance, insect resistance, drought resistance and quality of rice;

c). after selfing and selection for multiple generations, comparing the different lines of each generation, and selecting a better single plant for continuous selfing for multiple generations until the traits of the line are basically stable;

d). comparing different selected lines, and carrying out molecular marker detection screening again by using molecular markers related to high fecundity, disease resistance, insect resistance, drought resistance and quality of rice, to select a stable line with high yield performance, good traits of spikes and grains, strong resistance and molecular markers as a preferred line;

e). carrying out test-crossing on the preferred line as a male parent with different types of polyploid rice photo-thermo-sensitive genetic male sterile lines; and f). carrying out floristic comparison on different test-crossing group hybrids, and selecting a hybrid combination with good shape, strong resistance, strong combining ability and strong heterosis and a restorer line thereof through detections of morphological characteristics, combining ability and heterosis, wherein the restorer line is a tetraploid rice two-line restorer line.

Embodiment 4

Figure 6:
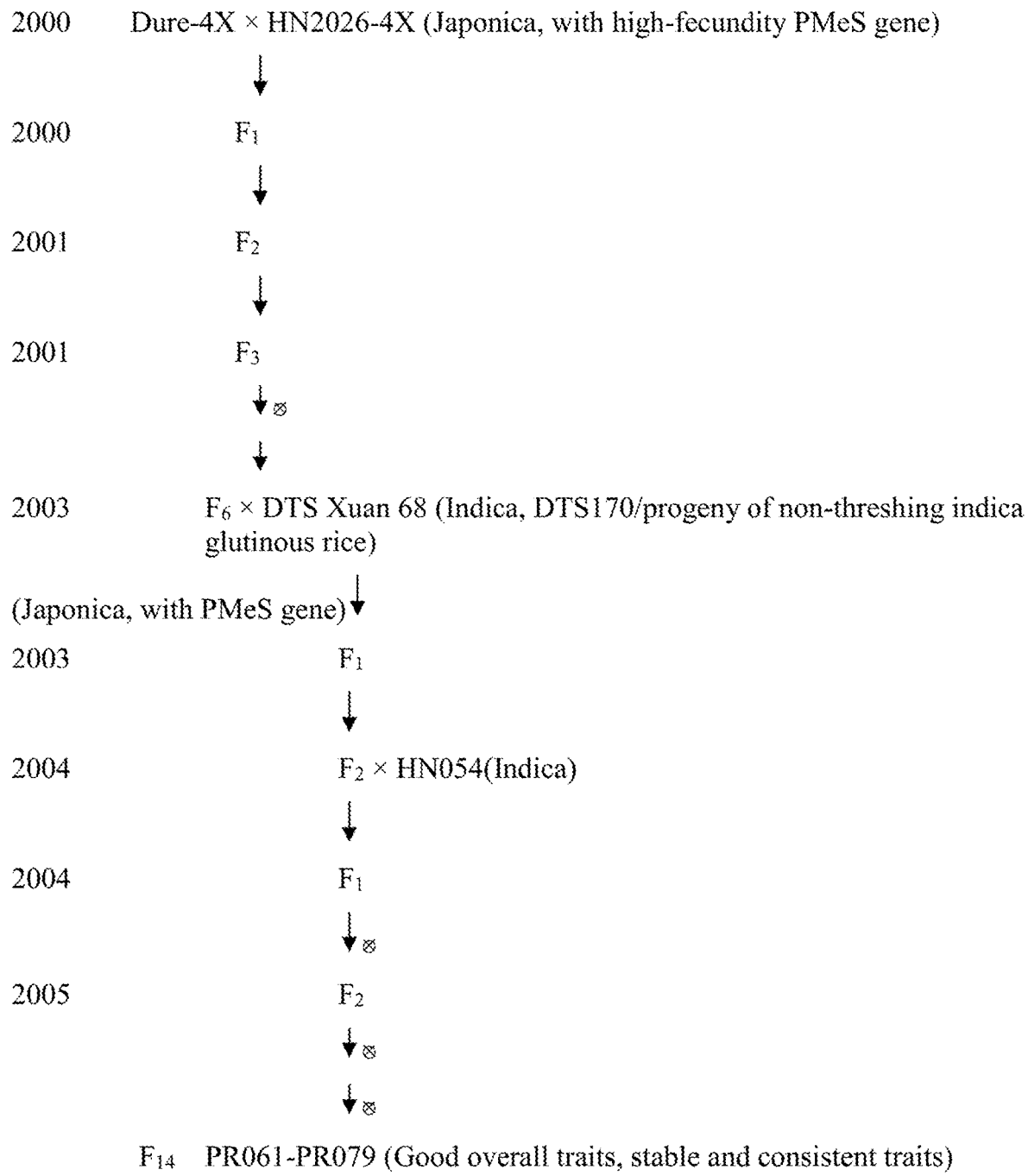
FIG. 6 shows PRO61-PR079 pedigree.

Breeding of tetraploid rice restorer line-PR061-PR079
PR061-PR079 pedigree is shown in FIG. 6.
Description of Breeding Process:

a). carrying out hybridization on the tetraploid japonica-cline type line Dure as a female parent and the tetraploid rice line HN2026 having PMeS gene as a male parent, and after continuous selfing of the hybrid progeny for 5 generations, then carrying out composite hybridization by using the tetraploid indica line—DTS Xuan 68 (DTS170/non-threshing indica glutinous rice) as a male parent;

b). selecting a single plant that meets the breeding goal in a targeted manner according to the polyploid rice ideal plant type and the characteristics of large spikes and big grains of polyploid rice, after selfing of composite hybridization hybrids for one generation, carrying out composite hybridization on fine line HN054 of tetraploid rice having PMeS gene, and then carrying out molecular marker detection screening on composite hybridization progeny by using the molecular markers related to high fecundity, disease resistance, insect resistance, drought resistance and quality of rice;

c). after selfing and selection for multiple generations, comparing the different lines of each generation, and selecting a single plant for continuous selfing for multiple generations until the traits of the line are basically stable;

d). comparing different selected lines, and carrying out molecular marker detection screening again by using molecular markers related to high fecundity, disease resistance, insect resistance, drought resistance and quality of rice, to select a stable line with high yield performance, good traits of spikes and grains, strong resistance and molecular markers as a preferred line;

e). carrying out test-crossing on the preferred line as a male parent with different types of polyploid rice photo-thermo-sensitive genetic male sterile lines; and f). carrying out floristic comparison on different test-crossing group hybrids, and selecting a hybrid combination with good shape, strong resistance, strong combining ability and strong heterosis and a restorer line thereof through detections of morphological characteristics, combining ability and heterosis, wherein the restorer line is a tetraploid rice two-line restorer line.

Embodiment 5

Figure 7:
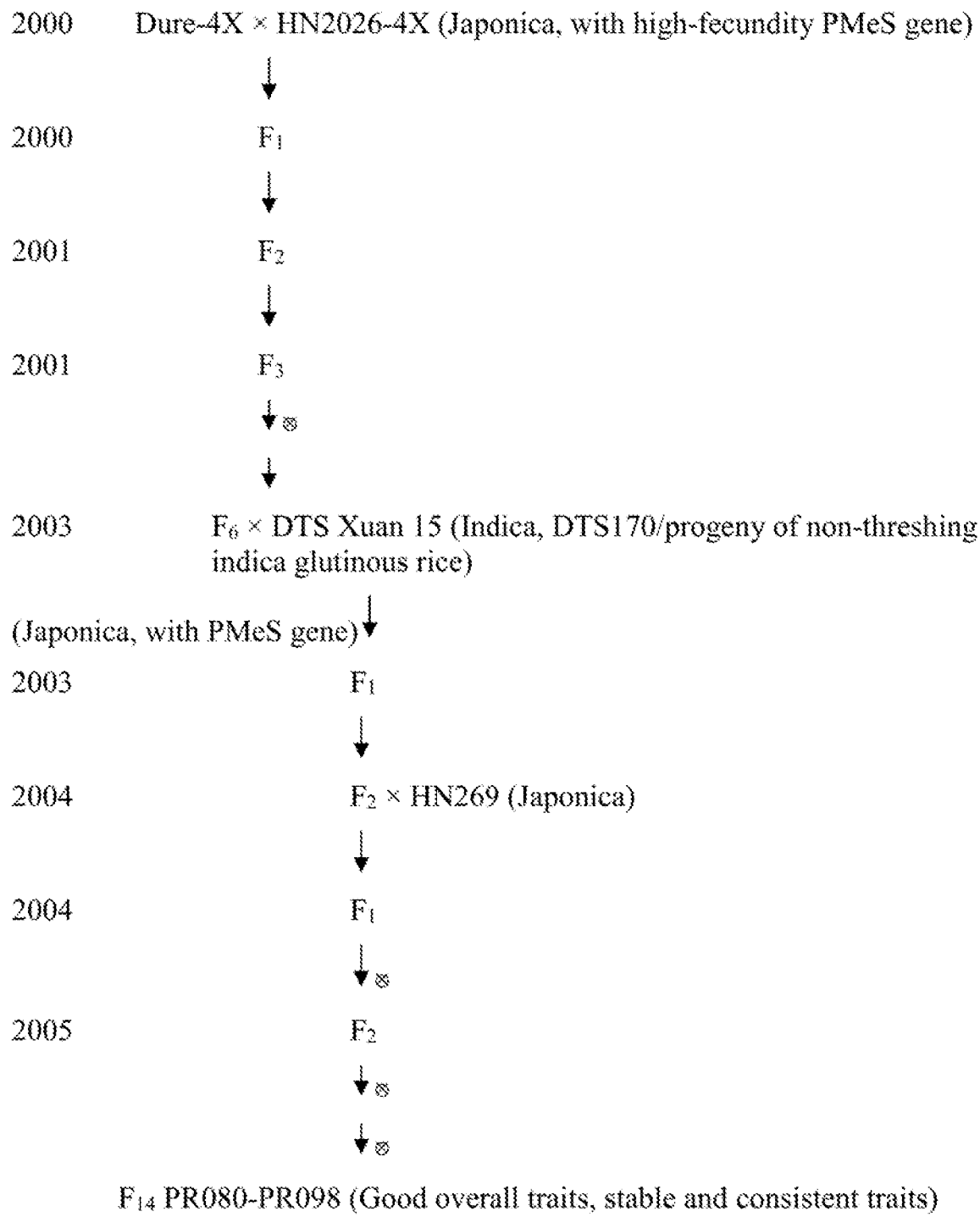
FIG. 7 shows PRO80-PR098 pedigree

Breeding of tetrapolid rice restorer line-PR080-PR098
PRO080-PR098 pedigree is shown in FIG. 7.
Description of Breeding Process:

a). carrying out hybridization on the tetraploid japonica-cline type line Dure as a female parent and the tetraploid rice line HN2026 having PMeS gene as a male parent, and after continuous selfing of the hybrid progeny for 5 generations, then carrying out composite hybridization by using the tetraploid indica line—DTS Xuan 15 (DTS170/non-threshing indica glutinous rice) as a male parent;

b). selecting a single plant that meets the breeding goal in a targeted manner according to the polyploid rice ideal plant type and the characteristics of large spikes and big grains of polyploid rice, after selfing of composite hybridization hybrids for one generation, carrying out composite hybridization on fine line HN269 of tetraploid rice having PMeS gene, and then carrying out molecular marker detection screening on composite hybridization progeny by using the molecular markers related to high fecundity, disease resistance, insect resistance, drought resistance and quality of rice;

c). after selfing and selection for multiple generations, comparing the different lines of each generation, and selecting a better single plant for continuous selfing for multiple generations until the traits of the line are basically stable;

d). comparing different selected lines, and carrying out molecular marker detection screening again by using molecular markers related to high fecundity, disease resistance, insect resistance, drought resistance and quality of rice, to select a stable line with high yield performance, good traits of spikes and grains, strong resistance and molecular markers as a preferred line;

e). carrying out test-crossing on the preferred line as a male parent with different types of polyploid rice photo-thermo-sensitive genetic male sterile lines; and f). carrying out floristic comparison on different test-crossing group hybrids, and selecting a hybrid combination with good shape, strong resistance, strong combining ability and strong heterosis and a restorer line thereof through detections of morphological characteristics, combining ability and heterosis, wherein the restorer line is a tetraploid rice two-line restorer line.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments are chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A breeding method of a polyploid rice two-line restorer line, comprising the following steps:
   (a) determining hybrid parents for breeding a restorer line, wherein the hybrid parents comprises a polyploid meiosis stability (PMeS) gene line, a restorer line that is capable of restoring a photo-thermo-sensitive genetic male sterile gene, and indica and japonica lines that have resistance;
   (b) carrying out hybridization on a tetraploid japonica line as a female parent and a tetraploid japonica line having the PMeS gene as a male parent, and then carrying out composite hybridization by using a tetraploid indica line as a male parent,
   wherein the tetraploid japonica line as the female parent is a japonica restorer line Dure-4X that is capable of restoring the photo-thermo-sensitive genetic male sterile gene and has resistance, and sample of seed of said Dure-4X is deposited under CCTCC No: P202103;
   wherein the tetraploid japonica line having PMeS gene as the male parent is Sg99012, and sample of seed of said Sg99012 is deposited under CCTCC No: P202108; and
   wherein the tetraploid indica line for the composite hybridization is a indica restorer line DTS Xuan 59 that is capable of restoring the photo-thermo-sensitive genetic male sterile gene and has resistance, and sample of seed of said DTS Xuan 59 is deposited under CCTCC No: P202102;
   (c) selecting a rice single plant that meets the breeding goal in a targeted manner according to the polyploid rice ideal plant type and the characteristics of large spikes and big grains of polyploid rice, then carrying out composite hybridization on the selected rice single plant and a fine line of tetraploid rice having PMeS gene, and carrying out preliminary screening on the composite hybridization progeny by using molecular marker detection, wherein the fine line of tetraploid rice having PMeS gene is HN172, and sample of seed of said HN172 is deposited under CCTCC No: P202104;
   (d) after selfing and selection for multiple generations, comparing different lines selected in each generation, and selecting a single plant with good traits for continuous selfing until the traits of the line are stable;
   (e) comparing the selected different lines obtained in step (d), and carrying out screening again by using the molecular marker detection, to select a stable line with high yield performance, good traits of spikes and grains, strong resistance and molecular markers as a preferred line;
   (f) carrying out test-crossing on the preferred line as a male parent with different types of polyploid rice photo-thermo-sensitive genetic male sterile lines; and
   (g) carrying out floristic comparison on different test-crossing group hybrids, and selecting a hybrid combination with good shape, strong resistance, strong combining ability and strong heterosis and a restorer line thereof through detections of morphological characteristics, combining ability and heterosis, wherein the restorer line is a tetraploid rice two-line restorer line named as PR003, and a representative sample of seed of said PR003 is deposited under CCTCC No: P202109.

2. The breeding method of a polyploid rice two-line restorer line according to claim 1, wherein the tetraploid rice two-line restorer line is screened through detections of molecular markers related to high fecundity, disease resistance, insect resistance, drought resistance and quality of rice.

3. A tetraploid rice two-line restorer line obtained by the breeding method of a polyploid rice two-line restorer line according to claim 1 being named as PR003, wherein the representative sample of seed of said PR003 is deposited under CCTCC No: P202109.

* * * * *